US011129579B2

(12) United States Patent
Lim et al.

(10) Patent No.: US 11,129,579 B2
(45) Date of Patent: Sep. 28, 2021

(54) DENTAL TREATMENT PLANNING APPARATUS AND METHOD USING MATCHING OF TWO-DIMENSIONAL MEDICAL IMAGE AND THREE-DIMENSIONAL MEDICAL IMAGE

(71) Applicant: GENORAY CO., LTD., Seongnam-si (KR)

(72) Inventors: Young Hyun Lim, Seongnam-si (KR); Wook Song, Seongnam-si (KR); Bong Goo Lee, Seongnam-si (KR)

(73) Assignee: GENORAY CO., LTD., Seongnam-si (KR)

( * ) Notice: Subject to any disclaimer, the term of this patent is extended or adjusted under 35 U.S.C. 154(b) by 0 days.

(21) Appl. No.: 16/719,628

(22) Filed: Dec. 18, 2019

(65) Prior Publication Data
US 2020/0187881 A1 Jun. 18, 2020

(30) Foreign Application Priority Data
Dec. 18, 2018 (KR) .................. 10-2018-0164498

(51) Int. Cl.
*A61B 6/14* (2006.01)
*A61B 5/00* (2006.01)
*A61B 6/00* (2006.01)

(52) U.S. Cl.
CPC .............. *A61B 6/14* (2013.01); *A61B 5/0077* (2013.01); *A61B 5/0088* (2013.01); *A61B 6/5247* (2013.01)

(58) Field of Classification Search
CPC ....... A61B 6/14; A61B 6/5247; A61B 5/0077; A61B 5/0088
See application file for complete search history.

(56) References Cited

U.S. PATENT DOCUMENTS 6,007,332 A * 12/1999 O'Brien ................ A61C 19/10
356/404
6,030,209 A * 2/2000 Panzera ................ A61K 6/15
433/26
(Continued)

FOREIGN PATENT DOCUMENTS

JP H11-9590 A 1/1999
JP 2006-204330 A 8/2006
(Continued)

OTHER PUBLICATIONS

Office Action of corresponding Korean Patent Application No. 10-2018-0164498—6 pages (dated Jun. 11, 2020).
(Continued)

*Primary Examiner* — David P Porta
*Assistant Examiner* — Djura Malevic
(74) *Attorney, Agent, or Firm* — Knobbe Martens Olson & Bear LLP

(57) ABSTRACT

Provided are a dental treatment planning apparatus and method using image matching. The dental treatment planning apparatus includes a two-dimensional image photographing unit configured to generate a two-dimensional medical image by photographing a head of a person being treated, a three-dimensional image photographing unit configured to generate a three-dimensional medical image by photographing teeth of the person being treated, an image converting unit configured to generate a converted image by photographing the three-dimensional medical image under a photographing condition of the two-dimensional medical image, and an image matching unit configured to generate a matched image by matching the converted image to one region of the two-dimensional medical image.

8 Claims, 10 Drawing Sheets

(56) References Cited

U.S. PATENT DOCUMENTS

| | | | | |
|---|---|---|---|---|
| 6,621,491 B1* | 9/2003 | Baumrind | A61C 9/0046 | 345/419 |
| 6,648,640 B2* | 11/2003 | Rubbert | A61C 7/00 | 433/24 |
| 7,027,642 B2* | 4/2006 | Rubbert | A61C 7/00 | 382/154 |
| 7,234,937 B2* | 6/2007 | Sachdeva | A61C 7/00 | 433/24 |
| 7,330,577 B2* | 2/2008 | Ernst | G01B 11/25 | 356/603 |
| 7,494,338 B2* | 2/2009 | Durbin | A61C 9/00 | 433/29 |
| 7,657,074 B2* | 2/2010 | Haras | A61B 6/032 | 382/131 |
| 7,698,068 B2* | 4/2010 | Babayoff | G01J 3/508 | 702/19 |
| 7,813,591 B2* | 10/2010 | Paley | A61C 19/04 | 382/285 |
| 7,878,804 B2* | 2/2011 | Korytov | A61B 6/14 | 433/24 |
| 8,009,890 B2* | 8/2011 | Nishide | G06T 5/002 | 382/131 |
| 8,199,988 B2* | 6/2012 | Marshall | G16H 50/30 | 382/128 |
| 8,340,466 B2* | 12/2012 | Kordass | G06T 7/521 | 382/287 |
| 8,386,061 B2* | 2/2013 | Violante | A61C 13/0004 | 700/98 |
| 8,571,281 B2* | 10/2013 | Wong | A61B 1/0638 | 382/128 |
| 8,633,445 B2* | 1/2014 | Star-Lack | A61B 6/4035 | 250/363.1 |
| 8,662,900 B2* | 3/2014 | Bell, III | G09B 23/28 | 434/263 |
| 8,665,257 B2* | 3/2014 | Ernst | A61C 9/006 | |
| 8,705,828 B2* | 4/2014 | Yang | G06T 11/005 | 382/131 |
| 8,989,469 B2* | 3/2015 | Fahimian | A61B 6/484 | 382/131 |
| 9,091,628 B2* | 7/2015 | Sezen | G01N 23/083 | |
| 9,348,973 B2* | 5/2016 | Pettersson | G16H 50/50 | |
| 9,412,166 B2* | 8/2016 | Getto | G09B 23/283 | |
| 9,504,538 B2* | 11/2016 | Sachdeva | A61C 5/77 | |
| 9,659,409 B2* | 5/2017 | Siebarth | A61B 5/745 | |
| 9,707,061 B2* | 7/2017 | Morales | A61C 9/0046 | |
| 9,808,326 B2* | 11/2017 | Masoud | A61C 7/002 | |
| 9,855,114 B2* | 1/2018 | Chen | G06T 7/75 | |
| 9,861,457 B2* | 1/2018 | Fisker | A61C 5/20 | |
| 9,934,360 B2* | 4/2018 | Lajoie | A61C 9/004 | |
| 10,010,387 B2* | 7/2018 | Esbech | G01J 3/508 | |
| 10,076,388 B2* | 9/2018 | Saliger | A61C 5/70 | |
| 10,206,757 B2* | 2/2019 | Pettersson | A61C 1/084 | |
| 10,245,126 B2* | 4/2019 | Korten | A61C 13/0004 | |
| 10,285,656 B2* | 5/2019 | Wang | A61B 6/08 | |
| 10,376,715 B2* | 8/2019 | Chen | A61N 5/1039 | |
| 10,470,855 B2* | 11/2019 | Morales | A61C 13/01 | |
| 10,485,638 B2* | 11/2019 | Salah | G01J 3/508 | |
| 10,667,887 B2* | 6/2020 | Rohaly | A61C 13/0004 | |
| 10,685,259 B2* | 6/2020 | Salah | G06K 9/6215 | |
| 10,753,734 B2* | 8/2020 | Tewes | A61B 1/247 | |
| 10,779,909 B2* | 9/2020 | Salah | A61C 7/002 | |
| 10,821,301 B2* | 11/2020 | Nishio | A61N 5/1049 | |
| 2001/0038705 A1* | 11/2001 | Rubbert | A61C 7/00 | 382/128 |
| 2004/0029068 A1* | 2/2004 | Sachdeva | A61C 9/0046 | 433/24 |
| 2005/0038669 A1* | 2/2005 | Sachdeva | G06Q 10/10 | 705/2 |
| 2005/0219242 A1* | 10/2005 | Anh | G06T 17/10 | 345/419 |
| 2006/0083422 A1* | 4/2006 | Ernst | G01B 11/25 | 382/154 |
| 2006/0154198 A1* | 7/2006 | Durbin | A61C 9/0053 | 433/29 |
| 2006/0177792 A1* | 8/2006 | Touchstone | A61C 19/10 | 433/26 |
| 2007/0189455 A1* | 8/2007 | Allison | A61B 6/5217 | 378/95 |
| 2007/0207441 A1* | 9/2007 | Lauren | A61C 13/0004 | 433/213 |
| 2007/0299338 A1* | 12/2007 | Stevick | A61B 5/113 | 600/425 |
| 2008/0193896 A1* | 8/2008 | Yang | A61C 13/0027 | 433/68 |
| 2008/0306379 A1* | 12/2008 | Ikuma | A61B 5/065 | 600/424 |
| 2009/0304302 A1* | 12/2009 | Kordass | G06T 7/521 | 382/276 |
| 2009/0305185 A1* | 12/2009 | Lauren | A61C 9/0053 | 433/29 |
| 2009/0316966 A1* | 12/2009 | Marshall | A61B 6/5217 | 382/128 |
| 2010/0284589 A1* | 11/2010 | Thiel | A61C 9/006 | 382/128 |
| 2011/0085713 A1* | 4/2011 | Yan | G06T 7/174 | 382/128 |
| 2011/0107270 A1* | 5/2011 | Wang | G16H 20/40 | 715/850 |
| 2011/0109616 A1* | 5/2011 | Ernst | A61C 9/006 | 345/419 |
| 2011/0255765 A1* | 10/2011 | Carlson | A61B 6/14 | 382/131 |
| 2011/0316994 A1* | 12/2011 | Lemchen | A61C 9/0053 | 348/66 |
| 2012/0015316 A1* | 1/2012 | Sachdeva | A61C 5/77 | 433/24 |
| 2012/0093280 A1* | 4/2012 | Konno | A61B 6/032 | 378/7 |
| 2012/0114208 A1* | 5/2012 | Hirasawa | G06T 7/337 | 382/131 |
| 2012/0123576 A1* | 5/2012 | Pettersson | G16H 50/50 | 700/98 |
| 2012/0148131 A1* | 6/2012 | Couch | A61B 6/583 | 382/131 |
| 2013/0051519 A1* | 2/2013 | Yang | G06T 11/005 | 378/19 |
| 2013/0057547 A1* | 3/2013 | Hwang | G06T 7/75 | 345/420 |
| 2013/0090547 A1* | 4/2013 | Bani-Hashemi | A61N 5/1039 | 600/411 |
| 2013/0286174 A1* | 10/2013 | Urakabe | A61B 1/247 | 348/66 |
| 2014/0080095 A1* | 3/2014 | Suttin | A61C 9/0053 | 433/202.1 |
| 2014/0147026 A1* | 5/2014 | Liu | G06T 7/344 | 382/131 |
| 2014/0147807 A1* | 5/2014 | Yau | A61C 1/084 | 433/173 |
| 2014/0308623 A1* | 10/2014 | Chang | A61C 13/0004 | 433/29 |
| 2015/0132716 A1* | 5/2015 | Kusch | A61B 5/055 | 433/140 |
| 2015/0289954 A1* | 10/2015 | Chang | A61C 13/0004 | 433/29 |
| 2015/0359614 A1* | 12/2015 | Sachdeva | A61B 6/032 | 433/8 |
| 2015/0374460 A1* | 12/2015 | Sachdeva | G16H 40/20 | 703/1 |
| 2016/0174918 A1* | 6/2016 | Wang | A61B 6/588 | 378/63 |
| 2017/0231731 A1* | 8/2017 | Korten | A61C 13/082 | 433/203.1 |
| 2017/0325689 A1* | 11/2017 | Salah | G06T 7/251 | |
| 2017/0325690 A1* | 11/2017 | Salah | A61B 5/742 | |
| 2018/0153485 A1* | 6/2018 | Rahmes | A61B 6/5241 | |
| 2018/0185125 A1* | 7/2018 | Salah | A61B 5/064 | |
| 2019/0026599 A1* | 1/2019 | Salah | G06K 9/6273 | |
| 2019/0133717 A1* | 5/2019 | Salah | A61B 5/064 | |

(56) References Cited

U.S. PATENT DOCUMENTS

2019/0147591 A1* 5/2019 Chang ................... G16H 50/50
                                                         382/128
2019/0308033 A1* 10/2019 Nishio ................. A61N 5/1039
2019/0362522 A1* 11/2019 Han ..................... A61B 5/7267

FOREIGN PATENT DOCUMENTS

| JP | 2009-195352 A | 9/2009 |
| JP | 2013-524948 A | 6/2013 |
| JP | 2014-104361 A | 6/2014 |
| JP | 2018-518213 A | 7/2018 |
| KR | 10-2011-0135323 A | 12/2011 |
| KR | 10-2017-0124962 A | 11/2017 |

OTHER PUBLICATIONS

Office Action of Japanese Patent Application No. 2019-228408—8 pages (Dec. 8, 2020).

* cited by examiner

DENTAL TREATMENT PLANNING APPARATUS AND METHOD USING MATCHING OF TWO-DIMENSIONAL MEDICAL IMAGE AND THREE-DIMENSIONAL MEDICAL IMAGE

STATEMENT REGARDING GOVERNMENT SPONSORED RESEARCH OR DEVELOPMENT

This work was supported by the Advanced Technology Center (ATC) Program funded by the Ministry of Trade, Industry and Energy (MOTIE, Korea) (10077361, Integrated System for Dental Diagnosis, Treatment Simulation & PSI (Patient Specific Instrument) Design).

CROSS-REFERENCE TO RELATED APPLICATION

This application claims priority to and the benefit of Korean Patent Application No. 2018-0164498, filed on Dec. 18, 2018, the disclosure of which is incorporated herein by reference in its entirety.

BACKGROUND

1. Field

The present disclosure relates to a dental treatment planning apparatus and method, and more particularly, to a dental treatment planning apparatus and method using matching of a two-dimensional medical image and a three-dimensional medical image.

2. Discussion of Related Art

A large-area computed tomography (CT) device that covers a relatively wide field of view (FoV) has an advantage of efficiently establishing a treatment plan of a practitioner due to an entire head of a person who is being treated being photographed as well as teeth of the person being treated. On the other hand, the large-area CT device is relatively expensive and thus is generally provided only in large hospitals.

The disclosure of this section is to provide background information relating to the invention. Applicant does not admit that any information contained in this section constitutes prior art.

SUMMARY

One aspect of the present invention is directed to providing an integrated process that can apply analysis information of a two-dimensional medical image to analysis of a three-dimensional medical image or apply analysis information of the three-dimensional medical image to analysis of the two-dimensional medical image.

Another aspect of the present invention is also directed to providing an integrated process that can establish a treatment plan on the basis of a two-dimensional medical image and at the same time establish a treatment plan on the basis of a three-dimensional medical image.

According to an aspect of the present invention, there is provided a dental treatment planning apparatus using matching of a two-dimensional medical image and a three-dimensional medical image, which includes a two-dimensional image photographing unit configured to generate a two-dimensional medical image by photographing a person being treated, a three-dimensional image photographing unit configured to generate a three-dimensional medical image by photographing the person being treated, an image converting unit configured to generate a converted image by photographing the three-dimensional medical image under a photographing condition of the two-dimensional medical image, and an image matching unit configured to generate a matched image by matching the converted image to one region of the two-dimensional medical image.

The dental treatment planning apparatus may further include a treatment plan establishing unit configured to provide an interface for a practitioner to perform at least one of image analysis, treatment plan establishment, and treatment device design of the person being treated using the matched image.

The two-dimensional image photographing unit may include an X-ray source configured to irradiate the person being treated with X-rays and a first image detecting unit on which the person being treated is projected by the irradiation with the X-rays to detect the two-dimensional medical image.

The image converting unit may include a second image detecting unit on which the three-dimensional medical image is projected to detect the converted image and a viewing camera configured to project the three-dimensional medical image onto the second image detecting unit.

The image converting unit may satisfy the photographing condition of the two-dimensional medical image by adjusting at least one of a position and an angle of the viewing camera, a position of the second image detecting unit, and a position and a viewing angle of the three-dimensional medical image.

The image converting unit may satisfy the photographing condition of the two-dimensional medical image on the basis of information about intervals between the X-ray source, the person being treated, and the first image detecting unit.

The dental treatment planning apparatus may further include a matching error determining unit configured to determine a matching tolerance of the two-dimensional medical image and the converted image.

The image converting unit may regenerate the converted image by re-photographing the three-dimensional medical image when the matching tolerance is greater than or equal to a reference value.

The two-dimensional medical image may include a frontal two-dimensional medical image and a lateral two-dimensional medical image.

The dental treatment planning apparatus may further include a landmark displaying unit configured to form two landmark lines by applying landmarks respectively displayed on regions other than the one region of the frontal and lateral two-dimensional medical images to the three-dimensional medical image and configured to display an intersection of the two landmark lines on the three-dimensional medical image.

According to an aspect of the present invention, there is provided a dental treatment planning method using matching of a two-dimensional medical image and a three-dimensional medical image which includes generating a two-dimensional medical image by photographing a person being treated, generating a three-dimensional medical image by photographing the person being treated, generating a converted image by photographing the three-dimensional medical image under a photographing condition of the two-dimensional medical image, and generating a matched image by matching the converted image to one region of the two-dimensional medical image.

The dental treatment planning method may further include performing, by a practitioner, at least one of image analysis, treatment plan establishment, and treatment device design of the person being treated using the matched image.

The dental treatment planning method may further include determining a matching tolerance of the two-dimensional medical image and the converted image.

The dental treatment planning method may further include regenerating the converted image by re-photographing the three-dimensional medical image when the matching tolerance is greater than or equal to a reference value.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EMBODIMENTS

Figure 1:
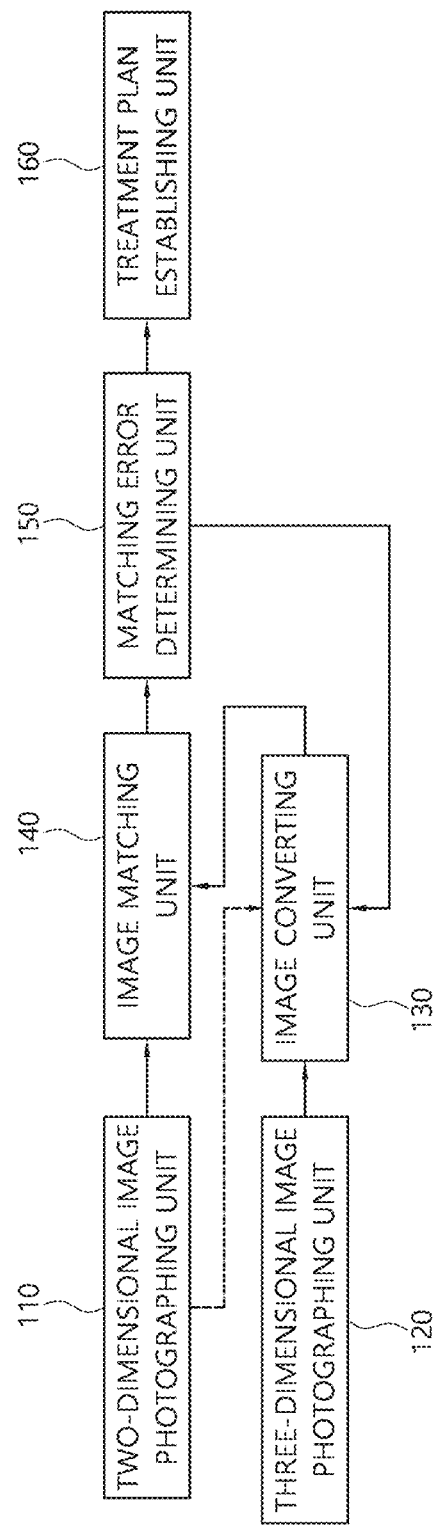
FIG. 1 is a block diagram of a dental treatment planning apparatus using image matching according to an embodiment of the present invention.

Hereinafter, embodiments of the present invention will be described in more detail with reference to the accompanying drawings. In this case, it should be noted that like reference numerals in the accompanying drawings denote like elements. However, detailed descriptions of well-known functions or configurations that unnecessarily obscure the gist of the present invention in the following explanations and accompanying drawings will be omitted.

In most small hospitals, a treatment plan of a practitioner is established by photographing only a teeth region of a person being treated using a small-area CT device that covers a relatively small FoV in consideration of costs.

Accordingly, aspects of the present invention propose a method of matching a three-dimensional medical image generated by a CT device photographing teeth of a person being treated to a two-dimensional medical image generated by a cephalometric radiography device photographing a head of the person being treated.

However, since the two-dimensional medical image generated by the cephalometric radiography device photographing the head of the person being treated is an image generated by positioning the head of the person being treated between an X-ray source and an image detecting unit and photographing, photographic distortion occurs. On the other hand, since photographic distortion occurring in the three-dimensional medical image photographed by the CT device is corrected and reconstructed in the CT device itself, in theory, the photographic distortion does not occur.

Therefore, it would be difficult to match the two-dimensional medical image in which photographic distortion occurs and the three-dimensional medical image in which photographic distortion is corrected.

Figure 2:
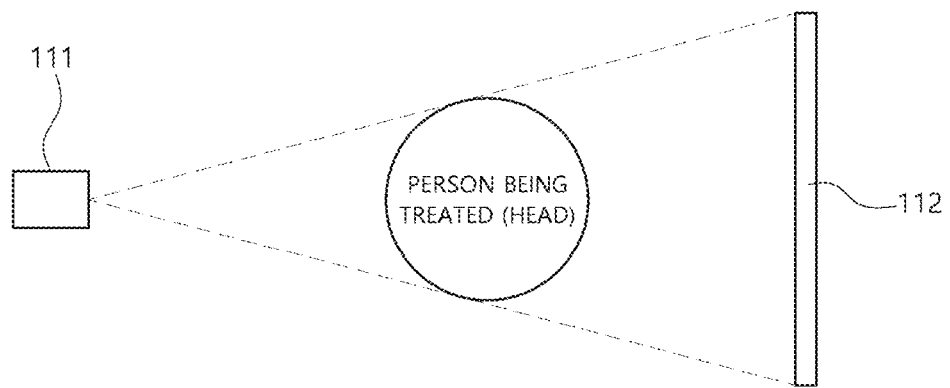
FIG. 2 is a block diagram of a two-dimensional image photographing unit of FIG. 1.

FIG. 1 is a block diagram of a dental treatment planning apparatus using matching of a two-dimensional medical image and a three-dimensional medical image according to an embodiment of the present invention, and FIG. 2 is a block diagram of a two-dimensional image photographing unit of FIG. 1.

As illustrated in FIG. 1, the dental treatment planning apparatus using the matching of the two-dimensional medical image and the three-dimensional medical image according to the embodiment of the present invention may include a two-dimensional image photographing unit 110, a three-dimensional image photographing unit 120, an image converting unit 130, an image matching unit 140, and a treatment plan establishing unit 160.

The two-dimensional image photographing unit 110 generates a two-dimensional medical image by photographing a person being treated under a specific photographing condition. Here, the two-dimensional image photographing unit 110 may be a cephalometric radiography device, but the present invention is not limited thereto, and the two-dimensional image photographing unit 110 may be any device as long as it can generate a two-dimensional image by photographing a person being treated.

Specifically, as illustrated in FIG. 2, the two-dimensional image photographing unit 110 may include an X-ray source 111 which irradiates the person being treated (e.g., a head) with X-rays and a second image detecting unit 112 on which the person being treated (e.g., the head) is projected by the irradiation with the X-rays to detect a two-dimensional medical image.

Figure 3:
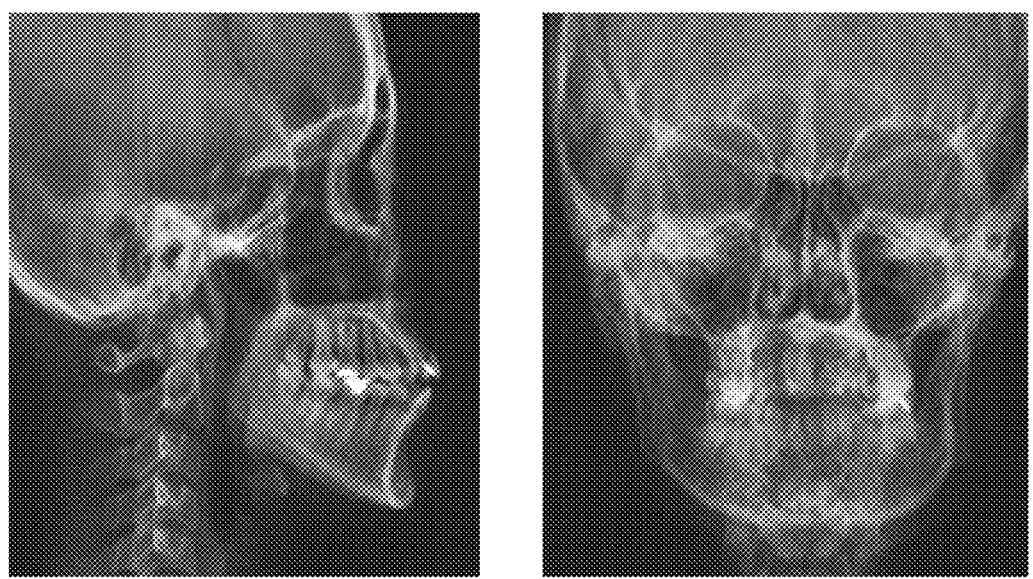
FIG. 3 shows diagrams of examples of two-dimensional medical images generated by the two-dimensional image photographing unit of FIG. 1 photographing a person being treated.
Figure 4:
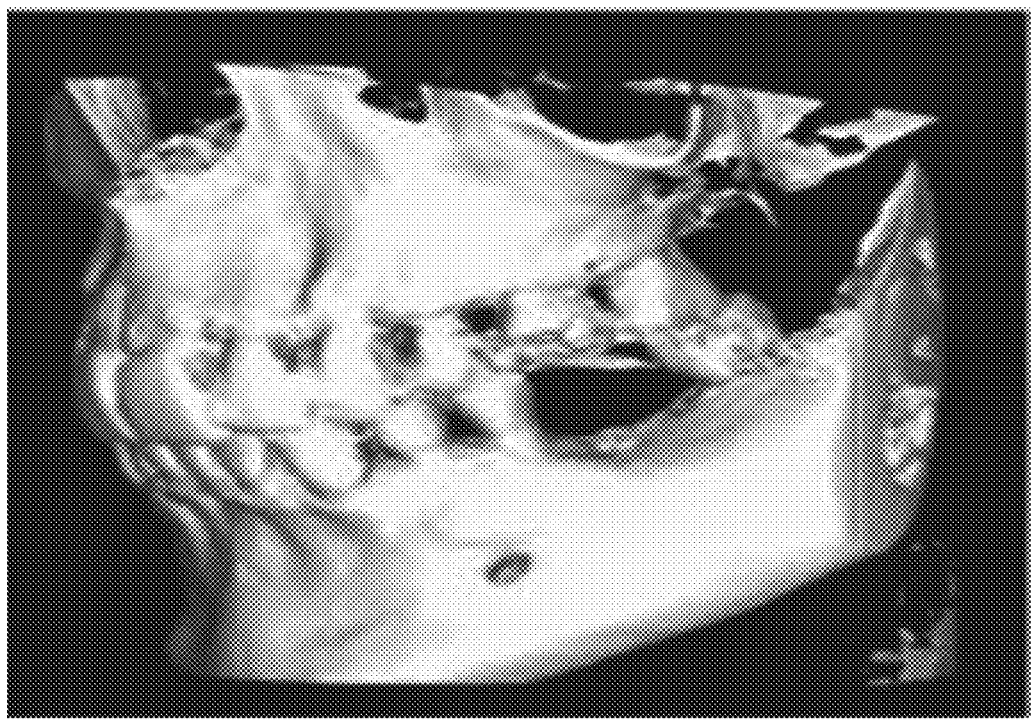
FIG. 4 is a diagram of an example of a three-dimensional medical image generated by a three-dimensional image photographing unit photographing the person being treated.

FIG. 3 shows diagrams of examples of two-dimensional medical images generated by the two-dimensional image photographing unit 110 of FIG. 1 photographing the person being treated, and FIG. 4 is a diagram of an example of a three-dimensional medical image generated by the three-dimensional image photographing unit 120 photographing the person being treated.

As illustrated in FIG. 3, the two-dimensional image photographing unit 110 may generate a lateral two-dimensional medical image (a) by photographing one side surface of a head of the person being treated and may generate a frontal two-dimensional medical image (b) by photographing a front surface of the head of the person being treated.

As illustrated in FIG. 4, the three-dimensional image photographing unit 120 generates a three-dimensional medical image by photographing teeth of the person being treated. Here, the three-dimensional image photographing unit 120 may be a computed tomography (CT) device, but the present invention is not limited thereto, and the three-dimensional image photographing unit 120 may be any device as long as it can generate a three-dimensional image by photographing a person being treated.

Meanwhile, a large-area CT device that covers a relatively wide field of view (FoV) generates a three-dimensional head image by photographing an entire head of a person being treated as well as teeth of the person being treated but is relatively expensive, and thus is generally provided only in large hospitals.

The three-dimensional image photographing unit 120 according to the embodiment of the present invention may generate a three-dimensional medical image by photographing the teeth region of the person being treated using a small-area CT device that covers a relatively narrow FoV and may match the generated three-dimensional medical image to the two-dimensional medical image generated by the two-dimensional image photographing unit 110, and thus an effect similar to that of the large-area CT device may be achieved at a relatively low cost.

Meanwhile, since the two-dimensional medical image generated by the two-dimensional image photographing unit 110 is an image generated by positioning the person being treated between the X-ray source 111 and the second image detecting unit 112 and photographing, as described above, photographic distortion may occur. However, since photographic distortion occurring in the three-dimensional medical image photographed by the three-dimensional image photographing unit 120 is corrected and reconstructed in the three-dimensional image photographing unit 120 itself, in theory, the photographic distortion does not occur. Therefore, it is difficult to match the two-dimensional medical image in which photographic distortion occurs and the three-dimensional medical image in which photographic distortion is corrected.

The image converting unit 130 according to one embodiment of the present invention generates a converted image by photographing the three-dimensional medical image under a photographing condition of the two-dimensional medical image photographing and matches the converted image to the two-dimensional medical image.

Figure 5:
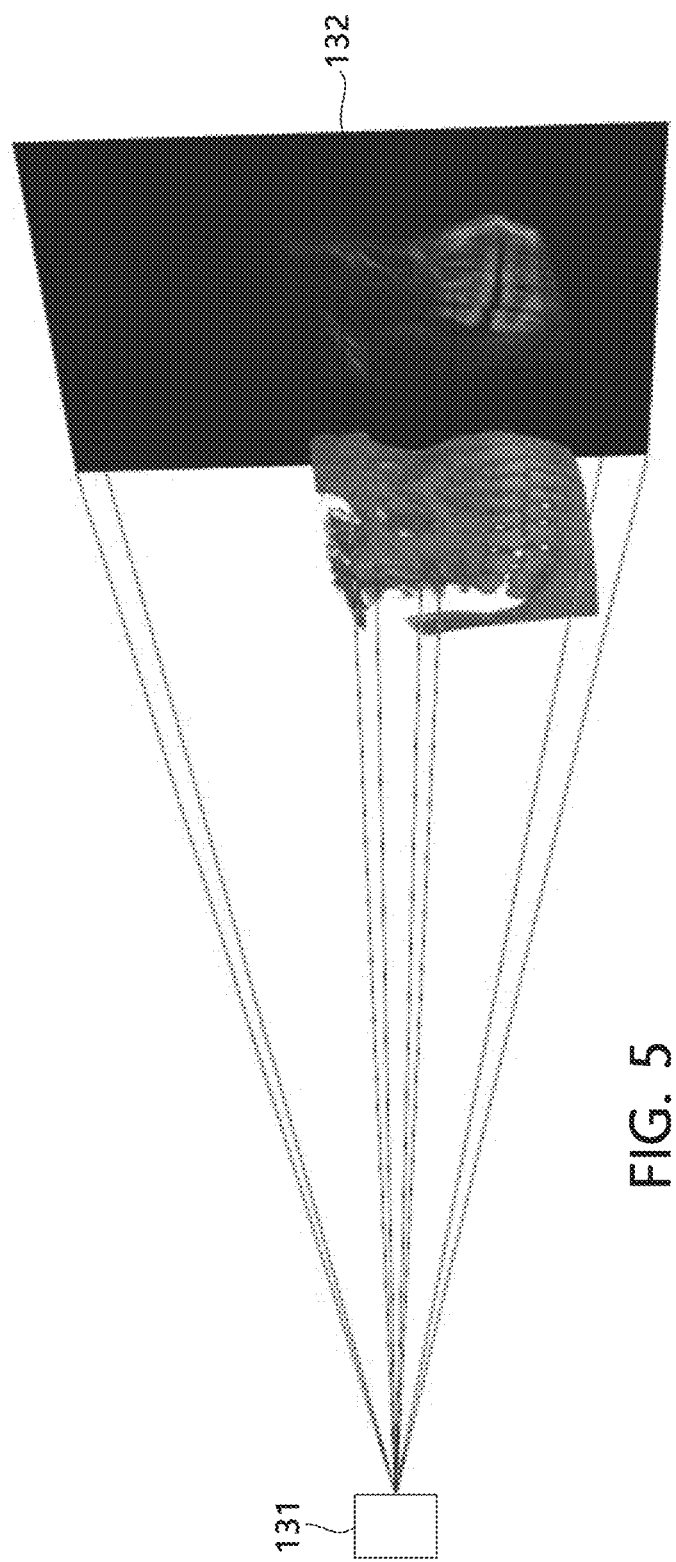
FIG. 5 is a detailed block diagram of an image converting unit of FIG. 1.

FIG. 5 is a detailed block diagram of the image converting unit of FIG. 1.

Specifically, as illustrated in FIG. 5, the image converting unit 130 may include a first image detecting unit 132 on which the three-dimensional medical image is projected to detect the converted image, and a viewing camera 131 which projects the three-dimensional medical image onto the first image detecting unit 132.

The image converting unit 130 may satisfy the photographing condition of the two-dimensional image photographing unit 110 on the basis of information about intervals between the X-ray source 111, the person being treated, and the second image detecting unit 112 when the two-dimensional image photographing unit 110 photographs the person being treated.

Further, the image converting unit 130 may satisfy the photographing condition of the head of the person being treated by adjusting at least one of a position and an angle of the viewing camera 131, a position of the first image detecting unit 132, and a position and a viewing angle of the three-dimensional medical image.

Specifically, the image converting unit 130 may satisfy the photographing condition of the two-dimensional medical image photographing by positioning the viewing camera 131, the three-dimensional medical image, and the first image detecting unit 132 at the same intervals as the intervals between the X-ray source 111, the person being treated, and the second image detecting unit 112 when the two-dimensional image photographing unit 110 photographs the head of the person being treated.

As described above, since the same photographic distortion as that in the two-dimensional medical image occurs in the converted image generated by being photographed under the photographing condition of the two-dimensional medical image, the matching of the two-dimensional medical image and the three-dimensional medical image may be relatively easily performed.

Figure 6:
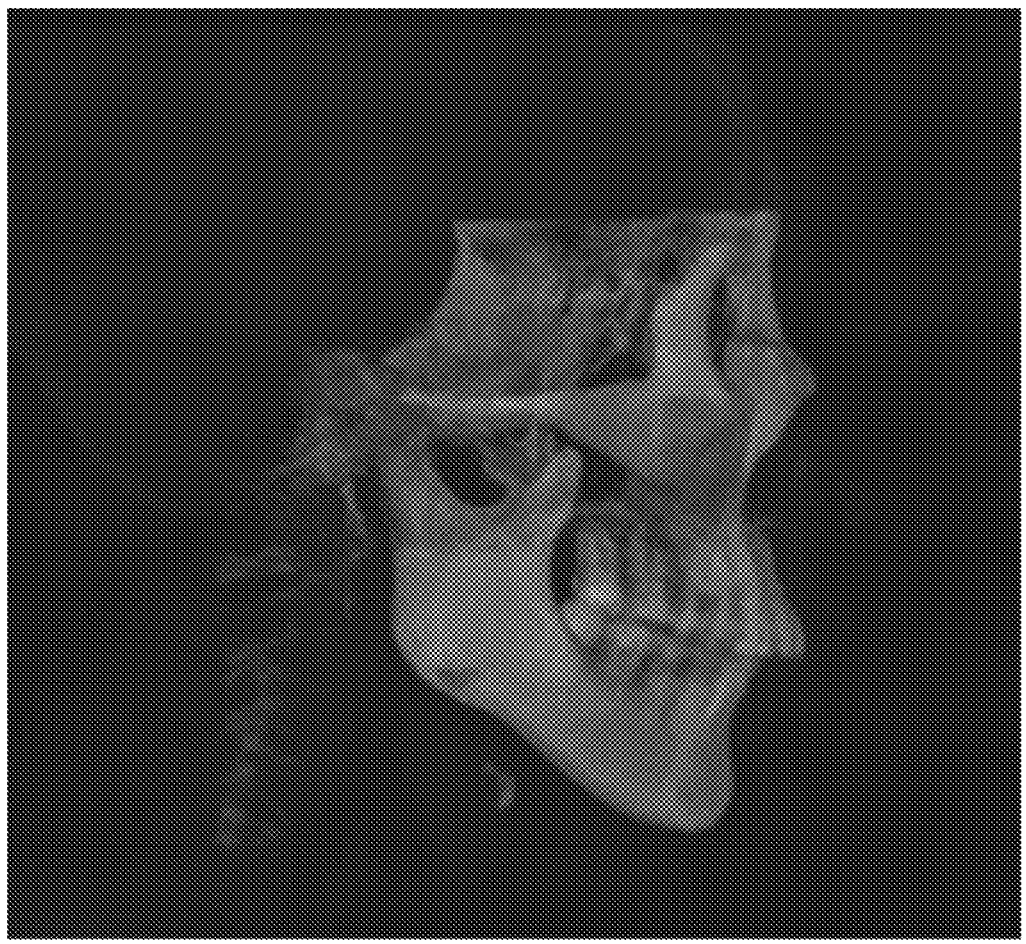
FIG. 6 is a diagram of an example of a matched image generated by an image matching unit of FIG. 1.

FIG. 6 is a diagram of an example of a matched image generated by the image matching unit 140 of FIG. 1.

As illustrated in FIG. 6, the image matching unit 140 generates a matched image by matching the converted image to one region of the two-dimensional medical image. Here, the matched image is an image in which the two-dimensional image and the three-dimensional image are combined, and the three-dimensional medical image is arranged in a region of the matched image corresponding to one region (e.g., a teeth region) of the person being treated, and the two-dimensional medical image is arranged in another region.

Referring to FIG. 1, the dental treatment planning apparatus using the matching of the two-dimensional medical image and the three-dimensional medical image according to the embodiment of the present invention may further include a matching error determining unit 150 which determines a matching tolerance of the two-dimensional medical image and the converted image.

The image converting unit 130 may regenerate the converted image by re-photographing the three-dimensional medical image when the matching tolerance determined by the matching error determining unit 150 is greater than or equal to a reference value. The above process may be repeatedly performed until the matching tolerance is less than the reference value. That is, the image converting unit 130 matches the converted image to the two-dimensional medical image using an iterative convergence matching method based on a two-dimensional medical image.

Referring to FIG. 3, the two-dimensional medical image generated by photographing using the two-dimensional image photographing unit 110 may include a frontal two-dimensional medical image and a lateral two-dimensional medical image. Accordingly, the above-described matching process may be performed twice focusing on the frontal two-dimensional medical image and the lateral two-dimensional medical image.

The treatment plan establishing unit 160 may provide a user interface for a practitioner to perform at least one of image analysis, treatment plan establishment, and treatment device design for the person being treated using the matched image. Here, the treatment plan establishing unit 160 may receive the matched image from the matching error determining unit 150 when the matching tolerance is less than the reference value.

Meanwhile, the two-dimensional image photographing unit 110 and the three-dimensional image photographing unit 120 may be provided in one piece of equipment together with each other or may be formed as separate modules. The image converting unit 130, the image matching unit 140, and the matching error determining unit 150 may be formed as a single module and provided to the treatment plan establishing unit 160 or provided to the two-dimensional image photographing unit 110 and the three-dimensional image photographing unit 120. Alternatively, the image converting unit 130, the image matching unit 140, and the matching error determining unit 150 may be provided as separate modules. The respective components may exchange image data by communication.

Figure 7:
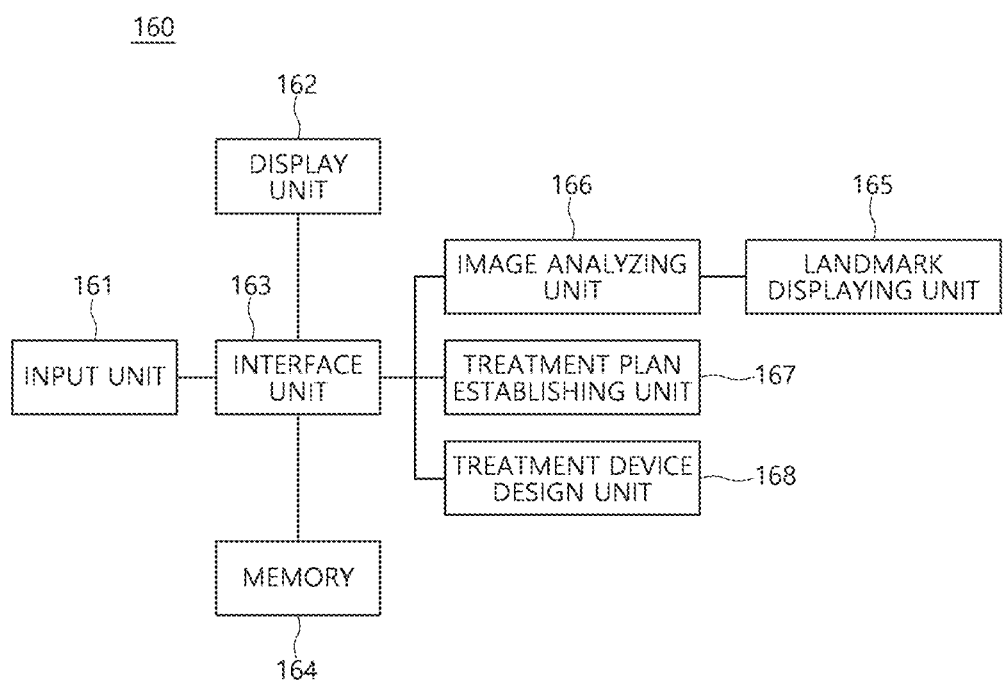
FIG. 7 is a detailed block diagram of a treatment plan establishing unit of FIG. 1.

FIG. 7 is a detailed block diagram of the treatment plan establishing unit 160 of FIG. 1.

Specifically, as illustrated in FIG. 7, the treatment plan establishing unit 160 may include an input unit 161, a display unit 162, an interface unit 163, a memory 164, a landmark displaying unit 165, an image analyzing unit 166, a treatment plan establishing unit 167, and a treatment device design unit 168.

Here, the treatment plan establishing unit 160 is an electronic device used by a practitioner who wants to operate on a person being treated and may be a tablet personal computer (PC), a computer, a laptop computer, or the like.

In addition, the treatment plan establishing unit 160 may perform communication with the two-dimensional and three-dimensional image photographing units 110 and 120 described above and a main server (not illustrated). Here, the treatment plan establishing unit 160 may transmit image data and a treatment plan to an external device through the main server. To this end, the treatment plan establishing unit 160 may perform wireless communication, such as fifth generation (5G) mobile telecommunication, Long-Term Evolution Advanced (LTE-A), Long-Term Evolution (LTE), Wideband Code Division Multiple Access (WCDMA), or Wi-Fi. Further, the treatment plan establishing unit 160 may perform wired communication, such as Universal Serial Bus (USB), High-Definition Multimedia Interface (HDMI), a Digital Visual Interface (DVI) cable, or the like.

The input unit 161 generates input data in response to an input of the practitioner. The input unit 161 includes a key pad, a dome switch, a touch panel, a jog and shuttle, a sensor, a touch key, a menu button, and the like.

The display unit 162 displays display data according to an operation of the treatment plan establishing unit 160. In particular, the display unit 162 displays a screen according to execution and operation of an application, a web page, and the like for performing image analysis, treatment plan establishment, and treatment device design for a person being treated.

To this end, the display unit 162 includes a liquid crystal display (LCD), a light-emitting diode (LED) display, an organic LED (OLED) display, a micro electro mechanical systems (MEMS) display, and an electronic paper display. Here, the display unit 162 may be combined with the input unit 161 and implemented as a touch screen.

The memory 164 may store operation programs of the treatment plan establishing unit 160, store an installation file such as an application for performing image analysis, treatment plan establishment, and treatment device designs for a person being treated, or store an access address of a web page or the like.

Further, the memory 164 stores image data for the person being treated and a treatment plan established in association with the image data. Here, the image data may be two-dimensional image data of a cephalometric image, which is a pixel-type image, a panorama format image, an image obtained by an input-and-output (IO) sensor, or an image obtained through X-rays, may be three-dimensional image data of a volume format image, a voxel format image, an image obtained by CT photographing, an image obtained by magnetic resonance imaging (MRI) photographing, an image obtained by ultrasound photographing, or the like, or may be matched image data obtained by matching two-dimensional image data and three-dimensional image data.

Figure 8:
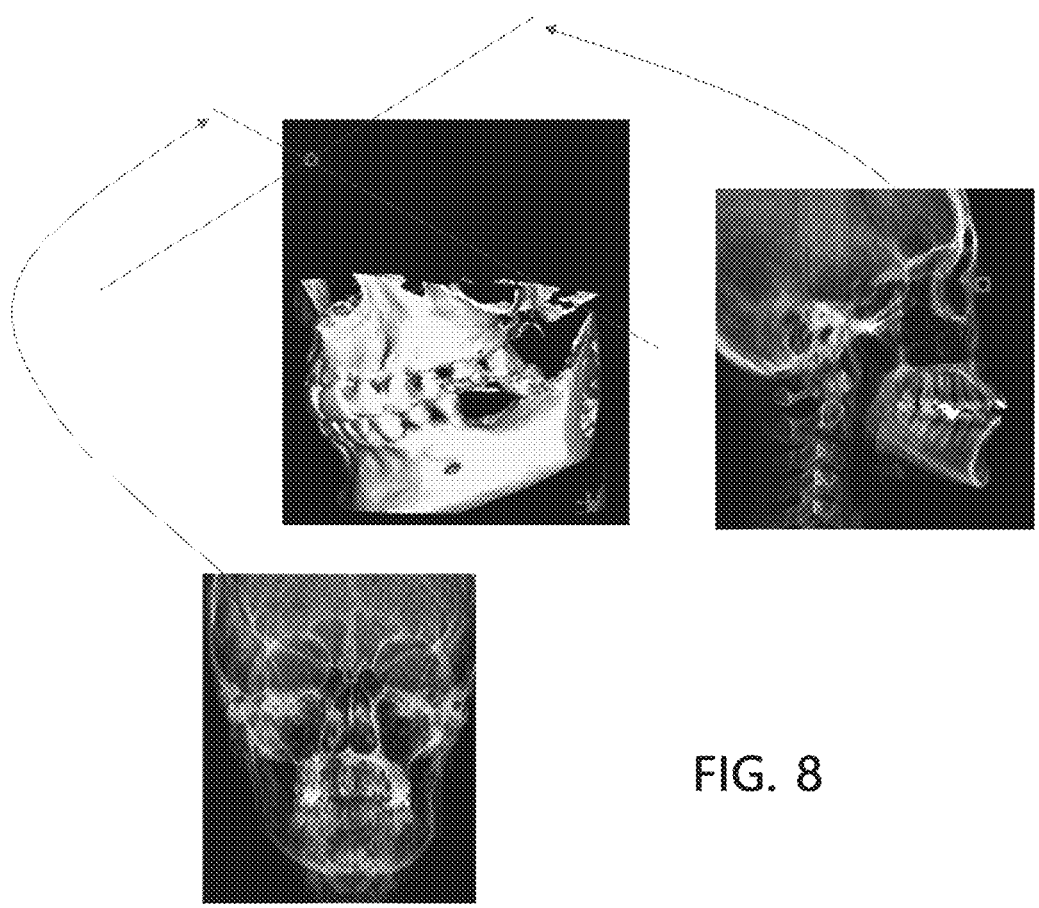
FIG. 8 is a diagram for describing a landmark displaying method of a landmark displaying unit of FIG. 7.
Figure 9:
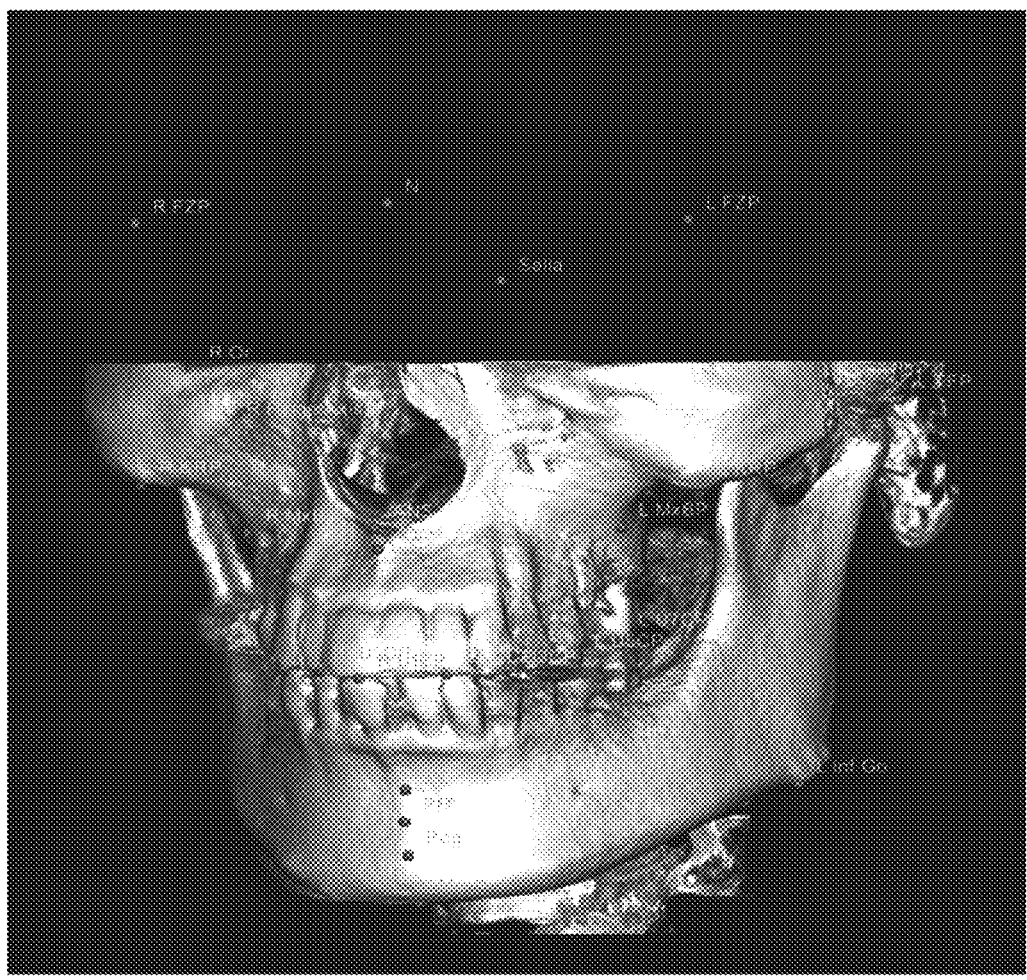
FIGS. 9 and 10 are diagrams illustrating landmarks which are displayed on a matched image by the landmark displaying unit of FIG. 7.
Figure 10:
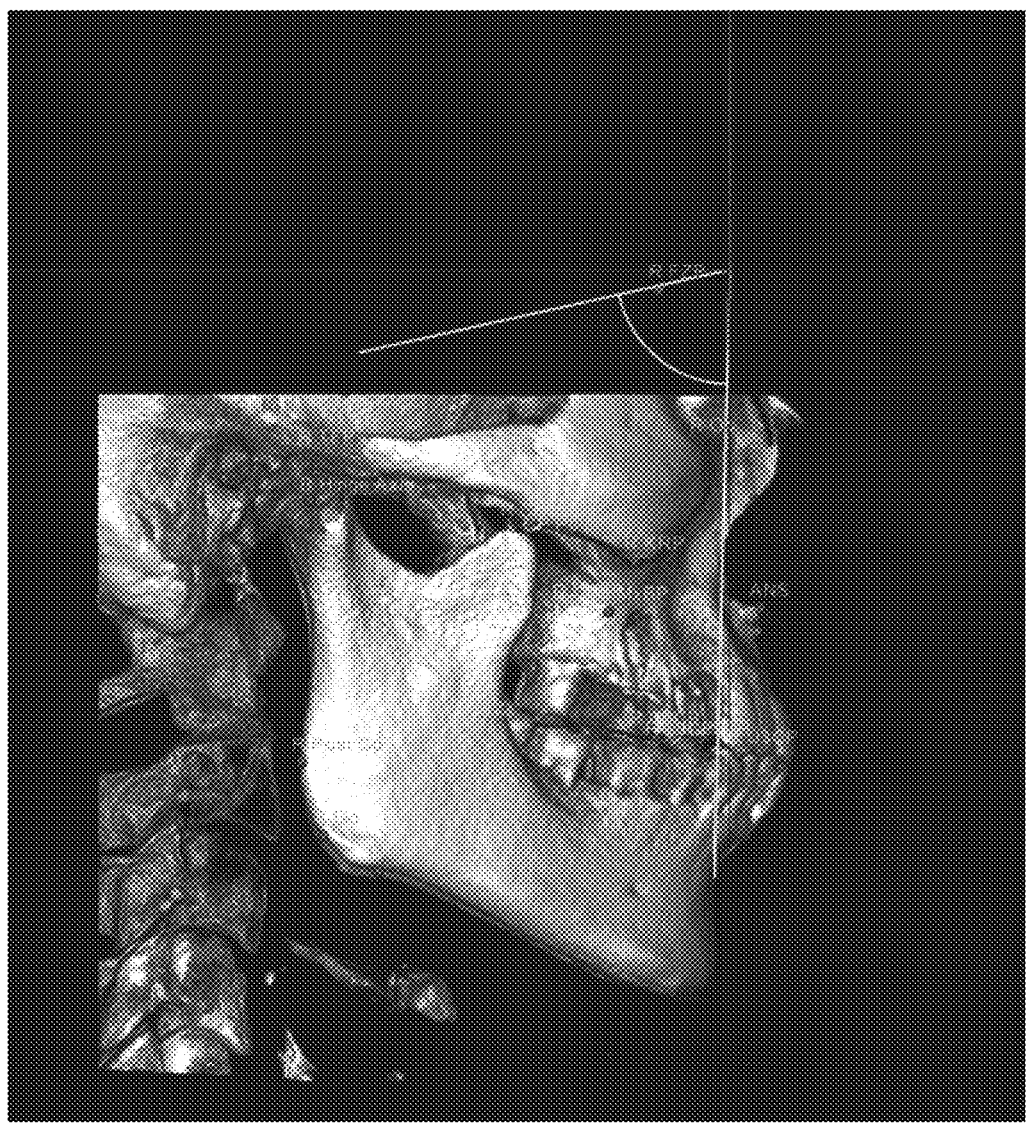

FIG. 8 is a diagram for describing a landmark displaying method of the landmark displaying unit of FIG. 7, and FIGS. 9 and 10 are diagrams illustrating landmarks which are displayed on the matched image by the landmark displaying unit of FIG. 7.

Referring to FIGS. 8 to 10, the landmark displaying unit 165 forms two landmark lines by applying landmarks respectively displayed on regions other than the teeth region of the frontal and lateral two-dimensional medical images to the three-dimensional medical image and displays an intersection of the two landmark lines on the three-dimensional medical image. Here, the landmarks are specific points necessary for image analysis.

The image analyzing unit 166 compares the landmarks displayed on the matched image with an average normal value based on a sex and dental age of the person being treated to generate an analysis result.

In the dental treatment planning apparatus using the image matching according to the embodiment of the present invention, image analysis is performed using the matched image, and thus an integrated process that can apply analysis information of the two-dimensional medical image to the analysis of the three-dimensional medical image or apply analysis information of the three-dimensional medical image to the analysis of the two-dimensional medical image may be provided.

The treatment plan establishing unit 167 may establish a plurality of treatment plans on the basis of the matched image and change at least one of the plurality of established treatment plans. Meanwhile, the treatment plans established by the treatment plan establishing unit 167 may be transmitted to an external device (e.g., a terminal or the like used in a dental laboratory).

In the dental treatment planning apparatus using the image matching according to the embodiment of the present invention, treatment plans are established using the matched image, and thus an integrated process that can establish the treatment plan on the two-dimensional medical image and at the same time establish the treatment plan on the three-dimensional medical image may be provided.

The treatment device design unit 168 may design treatment devices such as orthodontic devices, indirect bonding trays, occlusal wafers, dentures, and the like according to the treatment plans established by the treatment plan establishing unit 167.

In the dental treatment planning apparatus using the image matching according to the embodiment of the present invention, the image analysis, the treatment plan establishment, and the treatment device design are performed using one integrated process on the basis of the matched image, and thus treatment consultation times and treatment times may be shortened.

In addition, the number of X-ray and CT photographing operations may be reduced and thus the exposure of the person being treated to the X-rays may be minimized.

When the interface unit 163 receives an establishment signal for establishing the treatment plan for the person being treated from the input unit 161, the interface unit 163 calls an interface for the image analysis, the treatment plan establishment, and the treatment device design to display a main screen on the display unit 162.

Here, the interface refers to a user interface that can be checked by a user through execution and operation of an application, a web page, and the like for performing the image analysis, the treatment plan establishment, and the treatment device design.

The interface unit 163 appropriately provides a control signal received through the input unit 161 to the image analyzing unit 166, the treatment plan establishing unit 167, and the treatment device design unit 168 and allows the image analyzing unit 166, the treatment plan establishing unit 167, and the treatment device design unit 168 to perform an operation corresponding to the control signal.

When the interface unit 163 receives a call signal for calling image data for the person being treated from the input unit 161, the interface unit 163 retrieves the image data stored in the memory 164 on the basis of the call signal. The interface unit 163 calls the image data in association with the person being treated to display the image data on the main screen. In this case, the call signal may include a name of the person being treated, a patient number, or the like.

In addition, in the embodiment of the present invention, the image data is described as being stored in the memory 164, but the present invention is not limited thereto, and the image data may be stored in the main server. As described above, when the image data is stored in the main server, the treatment plan establishing unit 160 may call the image data from the main server to perform the image analysis, the treatment plan establishment, and the treatment device design.

Figure 11:
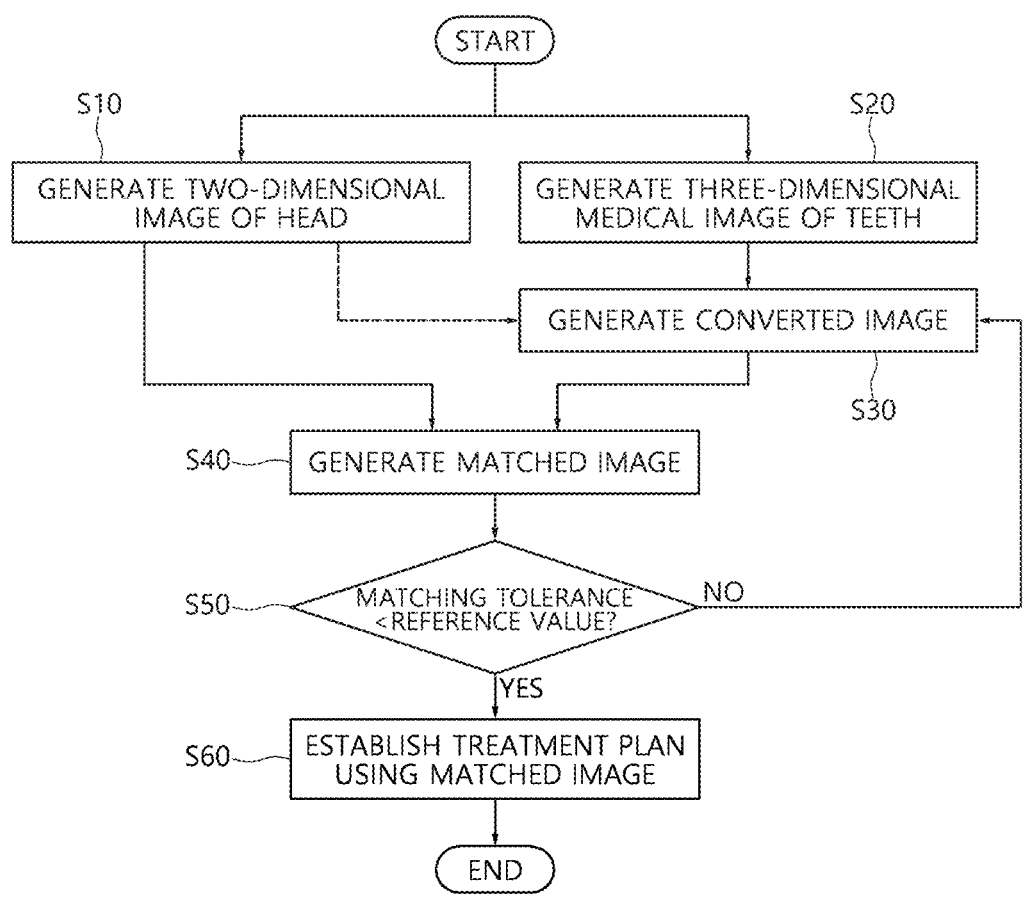
FIG. 11 is a flowchart of a dental treatment planning method using image matching according to an embodiment of the present invention.

FIG. 11 is a flowchart of a dental treatment planning method using image matching according to an embodiment of the present invention.

Hereinafter, a dental treatment planning method using matching of a two-dimensional medical image and a three-dimensional medical image according to an embodiment of the present invention will be described with reference to FIGS. 1 to 11, and the same contents as those of the dental treatment planning apparatus using the matching of the two-dimensional medical image and the three-dimensional medical image according to the embodiment of the present invention described above will be omitted.

The dental treatment planning method using the matching of the two-dimensional medical image and the three-dimensional medical image according to the embodiment of the present invention may include generating a two-dimensional medical image (S10), generating a three-dimensional medical image (S20), generating a converted image (S30), generating a matched image (S40), determining a matching tolerance (S50), and establishing a treatment plan using the matched image (S60).

First, a two-dimensional image photographing unit 110 generates a two-dimensional medical image by photographing a person being treated under a specific photographing condition (S10).

Specifically, when an X-ray source 111 irradiates a head of the person being treated with X-rays, the head of the person being treated is projected onto a second image detecting unit 112 and the two-dimensional medical image is generated.

Next, a three-dimensional image photographing unit 120 generates a three-dimensional medical image by photographing the person being treated under the photographing condition of the two-dimensional medical image (S20).

The three-dimensional image photographing unit 120 according to the embodiment of the present invention may generate a three-dimensional medical image by photographing a teeth region of the person being treated using a small-area CT device that covers a relatively small FoV and may match the three-dimensional medical image to the two-dimensional medical image generated by the two-dimensional image photographing unit 110, and thus an effect similar to that of the large-area CT device may be achieved at a relatively low cost.

Next, an image converting unit 130 generates a converted image by photographing the three-dimensional medical image under the photographing condition of the two-dimensional medical image (S30).

Specifically, when a viewing camera 131 projects the three-dimensional medical image onto a first image detecting unit 132, the three-dimensional medical image is projected onto the first image detecting unit 132 so that the converted image is generated.

As described above, the converted image generated by being photographed under the photographing condition of the two-dimensional medical image of the two-dimensional image photographing unit 110 has the same photographic distortion as the two-dimensional medical image, and thus the matching of the two-dimensional medical image and the three-dimensional medical image may be relatively easily performed.

Next, an image matching unit 140 generates a matched image by matching the converted image to a teeth region of the two-dimensional medical image (S40). Here, the matched image is an image in which the two-dimensional image and the three-dimensional image are combined, and the three-dimensional medical image is arranged in a region of the matched image corresponding to one region (e.g., the teeth region) of the person being treated and the two-dimensional medical image is arranged in another region.

Next, a matching error determining unit 150 determines a matching tolerance of the two-dimensional medical image and the converted image (S50).

Here, the image converting unit 130 may regenerate the converted image by re-photographing the three-dimensional medical image when the matching tolerance determined by the matching error determining unit 150 is greater than or equal to a reference value (S30). The above process may be repeatedly performed until the matching tolerance is less than the reference value. That is, the image converting unit 130 matches the converted image to the two-dimensional medical image using an iterative convergence matching method based on a two-dimensional medical image.

Next, a practitioner performs at least one of image analysis, treatment plan establishment, and treatment device design for the person being treated using the matched image when the matching tolerance determined by the matching error determining unit 150 is less than the reference value (S60).

As described above, in the dental treatment planning method using the matching of the two-dimensional medical image and the three-dimensional medical image according to the embodiment of the present invention, image analysis is performed using the matched image, and thus an integrated process that can apply analysis information of the two-dimensional medical image to the analysis of the three-dimensional medical image or apply analysis information of the three-dimensional medical image to the analysis of the two-dimensional medical image may be provided.

Further, in the dental treatment planning method using the matching of the two-dimensional medical image and the three-dimensional medical image according to the embodiment of the present invention, treatment plans are established using the matched image, and thus an integrated process that can establish the treatment plan on the two-dimensional medical image and at the same time establish the treatment plan on the three-dimensional medical image may be provided.

Further, treatment devices such as orthodontic devices, indirect bonding trays, occlusal wafers, dentures, and the like may be designed according to the established treatment plans.

Further, in the dental treatment planning method using the matching of the two-dimensional medical image and the three-dimensional medical image according to the embodiment of the present invention, the image analysis, the treatment plan establishment, and the treatment device design are performed using one integrated process on the basis of the matched image, and thus treatment consultation times and treatment times may be shortened.

In addition, the number of X-ray and CT photographing operations may be reduced and thus the exposure of the person being treated to the X-rays may be minimized.

According to the present invention, image analysis is performed using a matched image, and thus an integrated process that can apply analysis information of two-dimensional medical image to analysis of a three-dimensional medical image or apply analysis information of the three-dimensional medical image to analysis of the two-dimensional medical image can be provided.

Further, according to the present invention, treatment plans are established using a matched image, and thus an integrated process that can establish the treatment plan on the basis of the two-dimensional medical image and at the same time establish the treatment plan on the basis of the three-dimensional medical image can be provided.

Further, treatment devices such as orthodontic devices, indirect bonding trays, occlusal wafers, dentures, and the like can be designed according to the established treatment plans.

Further, according to the present invention, image analysis, treatment plan establishment, and treatment device design are performed using one integrated process on the basis of a matched image, and thus treatment consultation times and treatment times can be shortened.

In addition, the number of X-ray and CT photographing operations can be reduced and thus the exposure of the person being treated to the X-rays can be minimized.

Meanwhile, the embodiments disclosed in this specification and drawings are only examples to help understanding of the present invention and the present invention is not limited thereto. It is clear to those skilled in the art that various modifications based on the technological scope of the invention in addition to the embodiments disclosed herein can be made.

What is claimed is:

1. A dental treatment planning apparatus using matching of a two-dimensional medical image and a three-dimensional medical image, the dental treatment planning apparatus comprising:
    a computed tomography device configured to generate a two-dimensional medical image, in which photographic distortion occurs, by photographing a person being treated;
    a radiography device configured to generate a three-dimensional medical image by photographing the person being treated; and
    a computer configured to:
        generate a converted image by projecting the three-dimensional medical image so that the converted image has the same photographic distortion as the two-dimensional medical image,
        generate a matched image by matching the converted image to one region of the two-dimensional medical image,
        adjust at least one of a position of a first image detector detecting the converted image, a position and an angle of a viewing camera projecting the three-dimensional medical image to the first image detector, and a position and a viewing angle of the three-dimensional medical image so that the converted image has the same photographic distortion as the two-dimensional medical image, and
        regenerate the converted image until a matching tolerance between the two-dimensional medical image and the converted image is less than a reference value.

2. The dental treatment planning apparatus of claim 1, wherein the computer is configured to provide an interface for a practitioner to perform at least one of image analysis, treatment plan establishment, and treatment device design of the person being treated using the matched image.

3. The dental treatment planning apparatus of claim 1, wherein the computed tomography device includes:
    an X-ray source configured to irradiate the person being treated with X-rays; and
    a second image detector on which the person being treated is projected by the irradiation with the X-rays to detect the two-dimensional medical image.

4. The dental treatment planning apparatus of claim 1, wherein the computer is configured to determine a matching tolerance of the two-dimensional medical image and the converted image.

5. The dental treatment planning apparatus of claim 1, wherein the two-dimensional medical image includes a frontal two-dimensional medical image and a lateral two-dimensional medical image.

6. The dental treatment planning apparatus of claim 5, further comprising a display configured to form two landmark lines by applying landmarks respectively displayed on regions other than the one region of the frontal and lateral two-dimensional medical images to the three-dimensional medical image and configured to display an intersection of the two landmark lines on the three-dimensional medical image.

7. A dental treatment planning method using matching of a two-dimensional medical image and a three-dimensional medical image, the dental treatment planning method comprising:
    generating a two-dimensional medical image, in which photographic distortion occurs, by photographing a person being treated;
    generating a three-dimensional medical image, in which photographic distortion is corrected, by photographing the person being treated;
    generating a converted image by projecting the three-dimensional medical image so that the converted image has the same photographic distortion as the two-dimensional medical image;
    generating a matched image by matching the converted image to one region of the two-dimensional medical image;
    adjusting at least one of a position of a first image detector detecting the converted image, a position and an angle of a viewing camera projecting the three-dimensional medical image to the first image detector, and a position and a viewing angle of the three-dimensional medical image so that the converted image has the same photographic distortion as the two-dimensional medical image; and regenerating the converted image until a matching tolerance between the two-dimensional medical image and the converted image is less than a reference value.

8. The dental treatment planning method of claim 7, further comprising performing, by a practitioner, at least one of image analysis, treatment plan establishment, and treatment device design of the person being treated using the matched image.

* * * * *